(12) United States Patent
Goebel et al.

(10) Patent No.: US 9,546,953 B2
(45) Date of Patent: Jan. 17, 2017

(54) METHOD AND APPARATUS FOR REAL-TIME ANALYSIS OF CHEMICAL, BIOLOGICAL AND EXPLOSIVE SUBSTANCES IN THE AIR

(75) Inventors: Johann Goebel, Munich (DE); Matthias Kessler, Munich (DE)

(73) Assignee: Spherea GmbH, Ulm (DE)

( * ) Notice: Subject to any disclaimer, the term of this patent is extended or adjusted under 35 U.S.C. 154(b) by 2074 days.

(21) Appl. No.: 11/830,271

(22) Filed: Jul. 30, 2007

(65) Prior Publication Data

US 2009/0035183 A1 Feb. 5, 2009

(51) Int. Cl.
| | |
|---|---|
| *G01N 21/31* | (2006.01) |
| *G01N 33/22* | (2006.01) |
| *G01N 21/64* | (2006.01) |
| *G01N 33/00* | (2006.01) |
| *G01N 21/53* | (2006.01) |
| *G01N 21/03* | (2006.01) |
| *G01N 21/39* | (2006.01) |
| *G01N 24/08* | (2006.01) |
| *G01N 15/02* | (2006.01) |
| *G01N 21/17* | (2006.01) |

(52) U.S. Cl.
CPC ............ *G01N 21/53* (2013.01); *G01N 21/031* (2013.01); *G01N 21/31* (2013.01); *G01N 21/6486* (2013.01); *G01N 33/0057* (2013.01); *G01N 33/227* (2013.01); *G01N 15/0205* (2013.01); *G01N 24/084* (2013.01); *G01N 2021/1734* (2013.01); *G01N 2021/392* (2013.01)

(58) Field of Classification Search
USPC .............................. 422/82.05–82.11
See application file for complete search history.

(56) References Cited

U.S. PATENT DOCUMENTS

| | | | |
|---|---|---|---|
| 5,485,276 A | 1/1996 | Bien et al. | |
| 6,194,731 B1 | 2/2001 | Jeys et al. | |
| 6,538,728 B1* | 3/2003 | Stolle et al. | ................ 356/437 |
| 2005/0077476 A1* | 4/2005 | Poteet et al. | ............... 250/461.1 |
| 2006/0083350 A1* | 4/2006 | Gerndt et al. | ................ 378/70 |

FOREIGN PATENT DOCUMENTS

| | | |
|---|---|---|
| DE | 102 47 272 A1 | 4/2004 |
| DE | 103 06 900 A1 | 9/2004 |
| GB | 2 378 752 A | 2/2003 |
| WO | WO 97/49983 A1 | 12/1997 |

OTHER PUBLICATIONS

Ohzu, Akira. Remote Particle Counter Using Backscattered Light Imaging, Jpn. J. Appl. Phys. 45 (2006) pp. 1012-1014.*
International Search Report dated Jan. 21, 2009 (three (3) pages).

* cited by examiner

*Primary Examiner* — Neil N Turk
(74) *Attorney, Agent, or Firm* — Crowell & Moring LLP

(57) ABSTRACT

A device for real-time analysis of airborne chemical, biological and explosive substances has at least a gas analysis sensor, a fluorescence/luminescence sensor and a sensor for determining the particle size and number of particles. Each of the sensors is connected to a multireflection cell (multipass laser cell) as an open measurement path. In addition, the device also includes an evaluation unit for the real-time analysis of chemical, biological and explosive substances.

15 Claims, 3 Drawing Sheets

| Ionization | Fluorescence | Backscatter | | Result signature |
|---|---|---|---|---|
| A | B | C | | |
| • | • | • | all | 1 |
| • | • | - | Bacterial Spores | 2 |
| • | - | • | Susp'd Toxic Subst. | 3 |
| • | - | - | Particles (inorganic) | 4 |
| - | • | • | VOS's (toxic virus) | 5 |
| - | • | - | Virus | 6 |
| - | - | • | VC's (organic, inorganic) | 7 |
| - | - | - | None | 8 |

Fig. 3

METHOD AND APPARATUS FOR REAL-TIME ANALYSIS OF CHEMICAL, BIOLOGICAL AND EXPLOSIVE SUBSTANCES IN THE AIR

BACKGROUND AND SUMMARY OF THE INVENTION

The present invention relates to a method and apparatus for real-time analysis of chemical, biological and explosive substances in the air.

Known devices for detecting individual dangerous substances generally have a closed sample chamber for analyzing the substances, and the analysis itself takes several minutes. Devices for the detection of bacteria, viruses or other microparticles provide, for example, for filtering-out and marking of the corresponding particles before the latter can than be detected automatically.

German Patent Document DE 103 06 900 A1 discloses a spectrometer having a laser arrangement for analyzing gas. The spectrometer comprises a chamber for receiving a gas, a device for generating a potential drop in the chamber, a laser light source as well as an optical resonator which is formed by opposing mirrors or is constructed as a ring resonator. Inside the chamber, a laser beam is generated for ionizing the gas. An ion collector is used for the detection of accelerated ions.

A similar device is described in German Patent Document DE 102 47 272 A1, in which, however, instead of an optical resonator constructed by opposing mirrors, a multireflection cell is provided which has mirrors that are constructed such that the laser beam is reflected many times between the mirrors. As a result, the distance of the laser beam interacting with the gas is increased, which leads to a higher current at the ion collector. Because of the optical arrangement generated by means of the mirrors, a plurality of laser beams are formed which each extend between two reflection points, mutually intersect in a central area and fan out toward the mirrors.

One disadvantage of the known state of the art is that, as a rule, only one of many dangerous substance classes is covered by each of the respective devices. Furthermore, the known devices are not capable of detecting the substances directly from ambient air, without pre-enrichment. Moreover, the conventional sampling times, which are in the minutes range, cannot be used for certain applications, such as transit controls, portal monitoring, hazard monitoring, etc. In addition, the known solutions are frequently heavy and bulky have a high initial costs.

One object of the invention therefore, is to provide an improved device for real-time analysis of chemical, biological and explosive substances, in which dangerous substances, such as biopathogens, viruses, bacteria, spores, chemical warfare agents, explosives, toxic compounds and drugs can be detected and proven rapidly and precisely, in ambient air.

According to the invention, this object is achieved by the method and apparatus for real-time analysis of chemical, biological and explosive substances in the air according to the invention, which includes at least a gas analysis sensor, a fluorescence/luminescence sensor and a sensor for determining the size and number of particles. The sensors are each connected with a multireflection cell as an open measuring path, and the device also includes an evaluation unit.

As a result, the disadvantages of the state of the art techniques are avoided, and an improved solution is provided for real-time analysis of chemical, biological and explosive substances in the air. In particular, the invention rapidly and precisely detects and proves dangerous substances, such as biopathogens, viruses, bacteria, spores, chemical warfare agents, explosives, toxic compounds and drugs in the ambient air. The number of pathogens or radioactive particles can easily be determined. The invention thus achieves a relative concentration measurement which cannot be determined by means of state of the art sensors. Furthermore, the threat class types can be determined based on the ratio of dimensions, fluorescence signals and gaseous constituents of the measured particles.

One of the measurement principles of the present invention is based on spectroscopic gas sensor technology, which operates using the speed of ions during their movement under the influence of an electric drift field in the air. Based on the different mass and cross-section of the ions, it is possible to differentiate between individual substances. The signal is measured as an arrival time spectrum of different types of ions, as in time-of-flight spectroscopy, but without the requirement of bulky instrumentation, vacuum pumps, etc.

Such ion mobility spectroscopy (IMS) can be used for the present invention. Most known instruments used for this purpose operate by means of a membrane inlet system and radioactive ion sources. This protects the instruments against water, vapor and all other conceivable contaminations in the air. The ionization principle utilized by these known instruments is based on a charge transfer reaction mechanism, which is also called chemical ionization.

An important element of the present invention is the combination of a highly sensitive ion detection device with a highly selective laser-based ionization mechanism. The ionization process itself is a two-photon ionization step leading to a detailed ion spectrum which permits better selectivity of the ion formation stage and better sensitivity, down to the ppt (parts per trillion) range.

The analysis part of the ion mobility spectroscopy instrumentation is used to detect enzymatic reaction products, pyrolysis starting materials of biomolecules or chemicals of toxins.

On the other hand, each biological system or molecule in living cells exhibits a fluorescing reaction when it is irradiated by UV light. As a result, a component of the bio-aerosol detection device according to the present invention, specifically a tunable laser ionization source (TULIS), offers an excellent possibility for detecting the fluorescent reaction mechanisms in living cells.

Finally, the intense laser irradiation and the long measuring path of the device according to the invention offer a simple possibility of measuring light reflections of particles, that is, the backscatter. This signal can be used for detecting the number and the size of the particles.

The combination of the above-mentioned measuring systems is a part of the present invention. In particular, the invention includes: i) a miniaturized ion mobility sensor for detecting gaseous or chemical compositions; ii) a fluorescence unit for detecting biomolecules; and iii) a backscatter detection unit for detecting the number and the size of particles. A multireflection cell with a miniaturized tunable laser source forms a combining element of these components. The measuring unit is an open system, in which no delays occur between the sampling and the analysis.

The combination and integration of CCDs, the ion mobility spectrometer, the multireflection cell and the laser leads to a compact and integrated device.

The multireflection cell (multipass laser cell—MLC) is the sampling and connection point of the gas analysis sensor (IMS), of the fluorescence and/or luminescence sensor and of the sensor for measuring the particle size and the particle number. A laser beam is introduced into the multireflection cell, whose beam path is lengthened by several internal reflections between two mirrors.

The length of the multireflection cell is approximately 9 centimeters. The length of the beam path is increased to approximately 3 to 9 meters as a result of the mirrors, without major losses. The wavelength of the laser irradiation source which is used amounts to between 200 nm and 350 nm (preferably 260 nm to 270 nm), with a repetition frequency of 10 Hz to 50 Hz. The pulse duration of the laser source amounts to 2 ns, and the mean pulse energy is at approximately 60 µJ. For example, a passive Q-switched diode pump solid-state laser for the stimulation and ionization can be used as the laser irradiation source.

A miniaturized ion mobility spectrometer, which operates in linear and low-field regions, is connected with the multireflection cell. By using low-field IMS technology, shorter measuring times and more detailed spectra are achieved in comparison with the intense-field IMS technology. Because of the excellent signal-to-noise ratio, measurements of sub "parts per trillion" (ppt) can easily be achieved.

In addition, by using a selective two-photon-driven ionization process, a higher sensitivity and a significant reduction of undesirable influences can be achieved. This is an important component of the analysis part. The invention can thereby operate in a so-called open system without membranes or separation processes. As a result, higher sensitivity can be achieved relative to known systems, with low cross-over influences and a real-time measurement.

According to the invention, the laser emits infrared radiation which, however, extends into the UV range, by means of frequency modulation techniques. With an optical quasi-continuous wave output of more than 1.5 mW, the laser irradiation source is sufficient for detecting biological substances.

When the laser beam stimulates a photon absorption in the multireflection cell, the intensity of the emitted fluorescence signals is collected in a photo diode detection unit by way of suitable filters for the elimination of scattered light. When using a tunable laser, adjustable liquid-crystal filters (LCTFs) or spectrometers can be used to increase the output and achieve higher resolution.

Furthermore, improved detection characteristics can be achieved by the use of fluorochromes in connection with antibodies. Fluorochromes are fluorescing markers of a high quantum and stokes efficiency. Stokes efficiency means that the change between the stimulation wavelength and the emission wavelength is high; for example, up to 200 nm. As a result the filtering between the stimulation wavelength and the emission wavelength is clearly facilitated.

A particle backscatter sensor is combined with the multireflection cell because particles, aerosols, bacteria and spores generate an intensive backscatter signal when they meet the laser beam.

Because of the long beam path, a large number of reflection signals are generated perpendicular to the laser beam. Together with a CCD detector element, the particle size and number are determined therefrom. Furthermore, so-called "particle image velocimetry" (PIV) can be used. This software takes snapshots of the particle position at different times and computes a velocity model therefrom. PIV can be used for regulating and measuring the examined airflow and for computing the population numbers.

Volatiles of toxins (aerosol) or other types can be detected by means of the ion mobility spectroscopy analysis device.

In addition to a specific drift time, a substance-selective ionization process results in a real-time measurement with an increases resolution of the examined process.

Spores and bacteria can be detected by way of released volatiles of a pyrolysis reaction which occurs when the intense green or IR laser light is emitted into the MCL cell. For a better differentiation, the laser light can be supplied in a permanent or switched manner. Even smaller pyrolysis products of bacteria cell membranes can be detected in this fashion. Detectable volatiles may be ammonia and orthonitrophenols (ONP). Spores are detected by the observation of calcium dipicolinate (DPA content 5-15%) or picolinic acid (PA). The measurement can take place by means of ion mobility spectroscopy or fluorescing parts.

In the case of particle size species, such as bacteria, spores and aerosol, the laser irradiation is reflected and is detected by way of backscatter signals (LIDAR). The size and the number of the observed particles can then be used to differentiate, and an alarm is triggered starting at a certain threshold value.

Since viruses are small species of a size of between 10 and 300 nm, detection by using scattered signals is difficult. To detect viruses, they are charged with a voltage or are ionized by means of a laser source, so that they can be identified separately and by the electronic drift field of the ion mobility spectroscopy device.

Most biological warfare (BW) pathogens preferably have a geometry which enables them to spread in the environment. These drop-shaped suspended substances usually have a size of between 0.5-5 µm. In addition to these pathogens, there are further substances, such as stabilizers, solvents or additional chemicals. A large range of BW pathogens are identified by means of known solvents and chemicals according to a typical pattern.

An integrated electronic identification and interface module, which is provided for each of the corresponding sensors, operates while interacting with hardware coordinated with a signal processor and signal evaluation algorithms.

In ion mobility spectroscopy, measurements can be made down to a level which permits detections in the range of ppt. The signal to noise factors are in the low ppb range at approximately 100, and can easily be intensified by an algorithm. The concentration originating from BW is high, particularly when using our laser-desorbing phase of the vaporization.

Detection with a high sensitivity in the particle phase has three parts. The first is the intense laser irradiation together with the short distance to the starting point from which the measurement takes place—a circumstance which ensures overall good detection while interacting with the sensitivity. The second is the velocity measurement; and the third is based on the currently used short wavelength emanating from the radiation source, so that good sensitivity is also achieved during the detection of even small particles.

Due to the targeted use of a two-photon-driven stimulation, a much higher quantum gain is achieved than can be achieved when a stimulation is used that is driven by one photon.

Because of the resonance-amplified multiple-photon ionization (REMPI), the sensitivity of the ion mobility spectroscopy based on the laser is greater than in the case of those of the conventional type. As required, this can by further amplified by two or three color ionization processes.

By using different wavelengths to illuminate the particles, an effective change is carried out during differentiation of various types by means of the size and arrangement. In addition, high-resolution CCDs are used to receive the backscatter signals from different angles in order to obtain a multidimensional overall picture.

The use of a resonant two-photon-driven stimulation achieves better sensitivity than when non-resonant single-photon-driven stimulation steps are used. Furthermore, the pulsating feeding reduces the problems of overlapping with respect to the wavelengths of feeding and emission.

As mentioned above, the measuring time during the ion mobility spectroscopy detection is brief; the excellent signal-to-noise ratio leads to a so-called "single shut measure frame" (a measurement with a one-time exposure). This means that a measurement for the detection of the spectra takes 20 ms. Moreover, particle identification takes place very rapidly (<1 ms) and is only a function of the used CCD technology. For example, a CCD array can be used. Fluorescence detection is also very rapid (<20 ms) and is a function of the usable CCD and duplication/identification technique.

For all sensors, the repetition rates for the detection are between 25 ms up to 100 ms. This means that the longest measuring time is 100 ms; the shortest measuring time is 25 ms. Compared to the demanded measuring time (less than 1 min), these time frames have the result that between 600 and 2,400 measurements can be carried out per minute, achieving a significant breakthrough in improving signal systems and accumulation routines.

In addition, a nuclear radiation sensor may also be provided for detecting radioactive emissions, and may be constructed as a very small silicon drift detector.

Finally, a process according to the invention for the real-time analysis of chemical, biological, explosive and/or radioactive substances in the air by means of a device according to claim 1 has the following steps:

UV laser irradiation of a sample in the multireflection cell;
ionization of the sample, if possible, detecting of the charge, the mobility and the wavelength;
fluorescence measurement of the sample, if possible, detection of the color, the duration and the wavelength;
backscatter measurement of the sample, if possible, detection of the particle number and the particle size.

Other objects, advantages and novel features of the present invention will become apparent from the following detailed description of the invention when considered in conjunction with the accompanying drawings.

BRIEF DESCRIPTION OF THE DRAWINGS

FIG. 3 is a table of identification patterns.

DETAILED DESCRIPTION OF THE DRAWINGS

Figure 1:
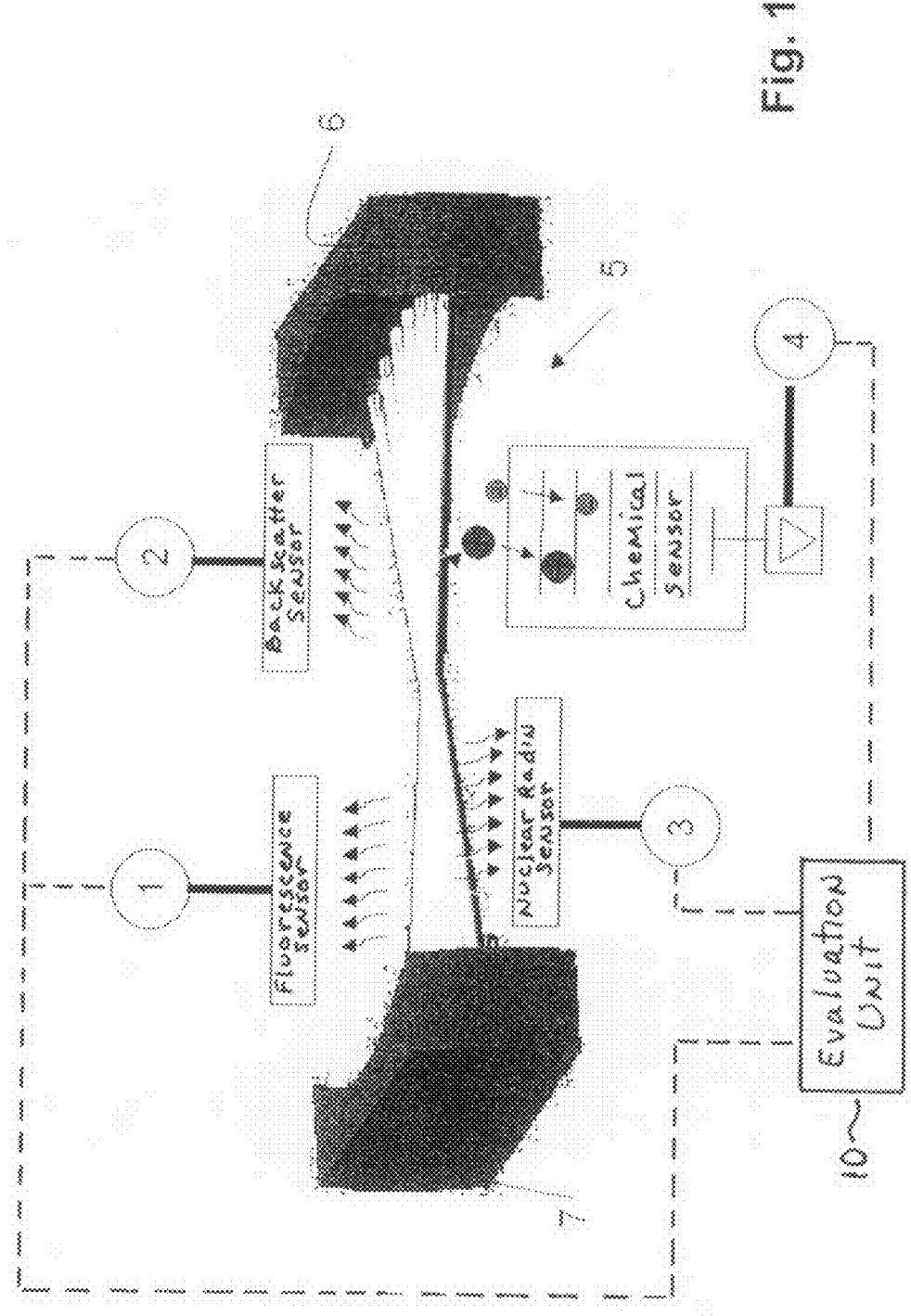
FIG. 1 is a schematic representation of a preferred embodiment of a device according to the invention for the real-time analysis of chemical, biological, explosive and radioactive substances in the air.

FIG. 1 is a schematic view of a preferred embodiment of a device according to the invention for real-time analysis of chemical, biological and explosive substances in the air. A laser unit 6 on the right emits a green light beam into a multireflection cell 5 for a better detection. The multireflection cell 5 is constructed as an open measuring path; that is, in contrast to known devices, ambient air can flow through it. In the present embodiment, the length of the measuring path of the essentially parallelepiped multireflection cell 5 is only 9 cm. At its longitudinal ends, the multireflection cell 5 has in each case several mirrors (not shown), which are disposed such that the laser beam is reflected multiple times between the mirrors. As a result the path of the laser beam interacting with the gas is increased to 6 m in the embodiment. Because of the optical arrangement generated by means of the mirrors, a plurality of laser beams are formed which each extend between two reflection points, which mutually intersect in a central area and which fan out toward the mirrors. In this case, the beam path of a single laser beam extends largely parallel.

The mirrors are made of silicon glass, having highly reflective surfaces for UV and green wavelengths. The surfaces of the mirrors consist of vapor-deposited non-conducting layers which are especially designed for the strains caused by laser irradiation. Each component of this device is mounted in an accurately fitting manner in a frame made of ceramics. An additional adjusting of the individual elements is not required.

An absorption detector 7 is arranged at the end of the multireflection cell situated opposite the laser unit 6, which is constructed as a tunable ultraviolet laser ionization source.

A fluorescence sensor 1 and a backscatter sensor 2 (which is constructed as a CCD detector element) each project from above into the measuring path of the multireflection cell 5. Furthermore, a nuclear radiation sensor 3 constructed in this embodiment as a silicon drift sensor is arranged below the measuring path. In addition, a chemical sensor 4, in the form of a laser IMS, is situated below the measuring path.

The sensors 1,2,3,4 are connected with an evaluation device in the form of a digital arithmetic logic unit 10, which evaluates the signals of the sensors 1,2,3,4 in real time and, as required, emits a danger alarm.

The particle sensor has a charge-coupled devices (CCD) which can pick up the backscatter of the laser signals from different angles.

The ion mobility technology has parallel plates with integrated drift field structures, an amplifier and several micro-mechanically manufactured elements.

The laser element may be constructed with one frequency, multiple frequencies or an optically parametric oscillator (OPO) having a tunable frequency range.

Each of the sensors has its own advantages. The chemical sensor 4 has a high sensitivity and selectivity. The fluorescence sensor 1 is an instrument of high efficiency for the identification of a plurality of biological species as a result of the special luminescence or fluorescence reaction.

Since each described sensor has the capability of carrying out a real-time measurement, the predictable overlap of time for the basic-pattern evaluation software is short. In such a case, there is the basically conceivable opportunity to examine the corresponding sample by means of other physical technologies.

Figure 2:
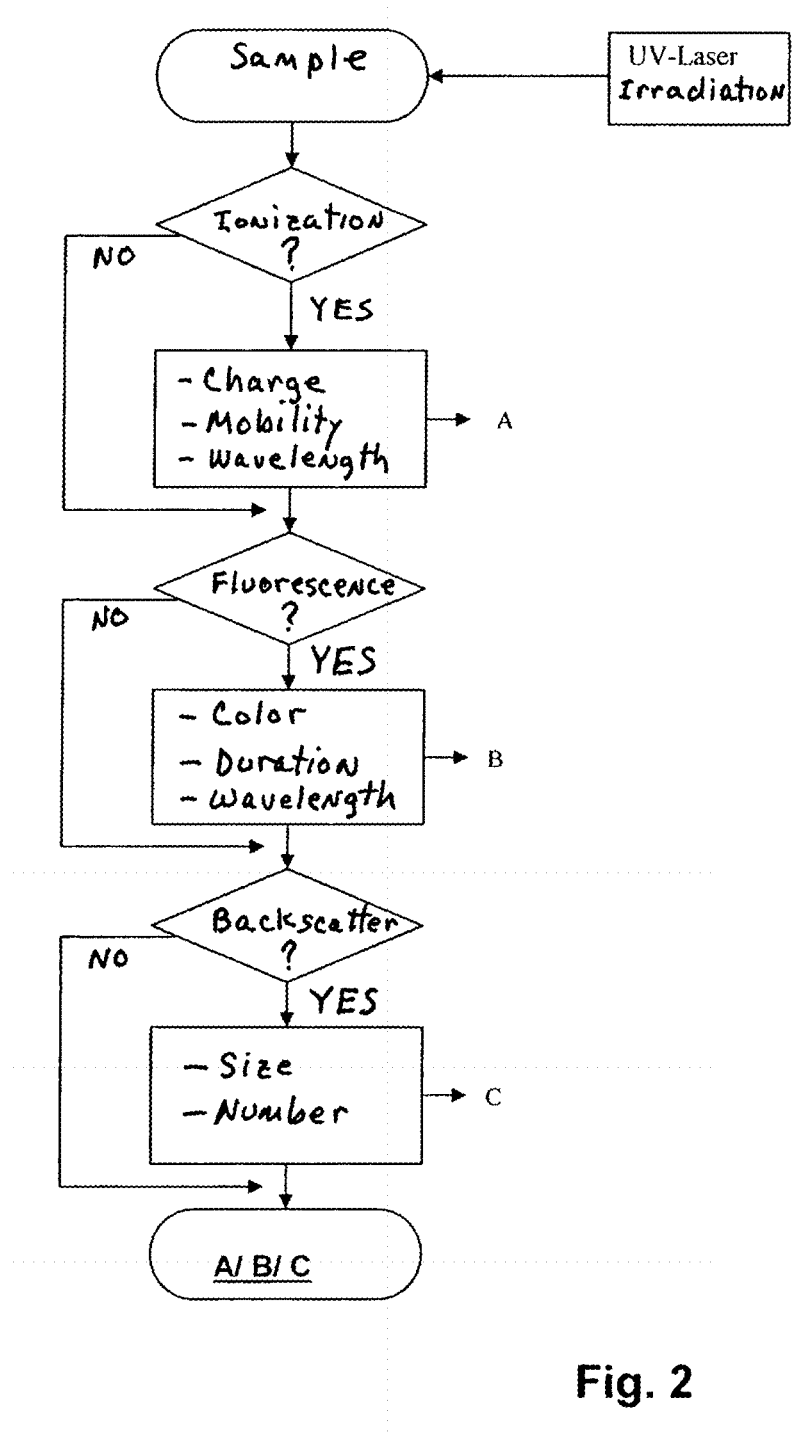
FIG. 2 is a flow chart that illustrates an identification algorithm for the device according to the invention for the identification of biological substances suspended in the air.

FIG. 2 is a flow chart showing an identification algorithm carried out by the evaluation unit. FIG. 3 is a table reflecting the identification pattern. The identification algorithm is based on the ionization A, the fluorescence B and the signal backscatter C, and leads to an output signal with eight basic patterns: for the ionization step (A), these include charge, mobility and wavelength, for the fluorescence step (B), color, duration, wavelength; and for the backscatter step (C), size and number. Each of these signals has its own special characteristics, such as concentration, wavelength, mobility, size, quantity, emission, etc., as shown in FIG. 3. The matrix relating to these criteria is weighted by means of the parameters of the measuring environment.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

LIST OF REFERENCE SYMBOLS

1 Fluorescence sensor
2 backscatter sensor
3 nuclear-radiation sensor
4 chemical sensor
5 multireflection cell (multipass laser cell)
6 laser unit
7 absorption detector
A ionization
B fluorescence
C backscatter

The invention claimed is:

1. A device for real-time analysis of chemical, biological and explosive substances in the air, the device comprising:
 a gas analysis sensor;
 a fluorescence/luminescence sensor;
 a sensor for determining a number and a size of particles; and
 an evaluation unit connected to receive an output of each of the gas analysis sensor, the fluorescence/luminescence sensor, and the sensor for determining the number and the size of particles; wherein:
 the gas analysis sensor, the fluorescence/luminescence sensor, and the sensor for determining the number and the size of particles are each operationally coupled with a multireflection cell as an open measuring path through which the chemical, biological and explosive substances flow in the air,
 the multireflection cell comprises a first minor arranged at a first longitudinal end of the multireflection cell and a second mirror arranged at a second longitudinal end of the multireflection cell, such that a laser beam is reflected a plurality of times between the first and second longitudinal ends of the multireflection cell to form a beam path,
 segments of the laser beam are formed between the first and second longitudinal ends of the multireflection cell, the segments of the laser beam substantially intersect in a central area of the multireflection cell, and the segments of the laser beam fan out toward the first and second longitudinal ends of the multireflection cell, and
 each of the gas analysis sensor, the fluorescence/luminescence sensor, and the sensor for determining the number and the size of particles performs measurements of signals from portions of the chemical, biological and explosive substances that are positioned at a same location along the beam path.

2. The device for the real-time analysis according to claim 1, further comprising a nuclear-radiation sensor for analyzing radioactive substances.

3. The device for real-time analysis according to claim 1, wherein the gas analysis sensor comprises a laser ion mobility spectroscopy device.

4. The device for real-time analysis according to claim 1, wherein the multireflection cell has a tunable UV laser irradiation source.

5. The device for real-time analysis according to claim 4, wherein a wavelength of the laser irradiation source is between 200 nm and 350 nm.

6. The device for real-time analysis according to claim 4, wherein a wavelength of the laser irradiation source is between 260 nm to 270 nm.

7. The device for real-time analysis according to claim 1, wherein a repetition frequency of a laser irradiation source of the laser beam is between 10 Hz and 50 Hz.

8. The device for real-time analysis according to claim 1, wherein the length of the beam path in the multireflection cell is 3 m to 9 m.

9. The device for real-time analysis according to claim 1, wherein the length of the beam path in the multireflection cell is 6 m.

10. The device for real-time analysis according to claim 1, wherein the sensor for determining the number and the size of the particles comprises a backscatter sensor.

11. The device for real-time analysis according to claim 2, wherein the nuclear-radiation sensor comprises a silicon drift detector.

12. Apparatus for real-time analysis of airborne chemical, biological and explosive substances, the apparatus comprising:
 a gas analysis sensor;
 a sensor for detecting at least one of fluorescence and luminescence;
 a particle sensor for measuring a number and a size of particles;
 a multireflection cell to which the gas analysis sensor, the sensor for detecting at least one of fluorescence and luminescence, and the particle sensor are at least operationally coupled;
 a laser radiation source arranged to emit laser radiation into the multireflection cell; and
 an evaluation unit coupled to receive output signals from each of the gas analysis sensor, the sensor for detecting at least one of fluorescence and luminescence, and the particle sensor; wherein:
 the particle sensor and the sensor for detecting at least one of fluorescence and luminescence are positioned to detect interaction between the laser radiation and a sample present in the multireflection cell,
 the multireflection cell is constructed as an open measuring path, which is open to a surrounding ambient atmosphere, and through which the airborne chemical, biological and explosive substances flow,
 the multireflection cell comprises a first minor arranged at a first longitudinal end of the multireflection cell and a second mirror arranged at a second longitudinal end of the multireflection cell, such that a laser beam is reflected a plurality of times between the first and second longitudinal ends of the multireflection cell to form a beam path,
 segments of the laser beam are formed between the first and second longitudinal ends of the multireflection cell, the segments of the laser beam substantially intersect in a central area of the multireflection cell, and the segments of the laser beam fan out toward the first and second longitudinal ends of the multireflection cell, and
 each of the gas analysis sensor, the sensor for detecting at least one of fluorescence and luminescence, and the particle sensor performs measurements of signals from portions of the chemical, biological and explosive substances that are positioned at a same location along the beam path.

13. The apparatus according to claim 12, wherein the gas analysis sensor comprises a low field ion mobility spectroscopy sensor which utilizes a laser based resonance amplified multiple photon ionization mechanism.

14. The apparatus according to claim 12, wherein the particle sensor and the sensor for detecting at least one of fluorescence and luminescence comprise a CCD array.

15. The apparatus according to claim 12, wherein the evaluation unit analyzes an output signal from each of the gas analysis sensor, the sensor for detecting at least one of fluorescence and luminescence, and the particle sensor, and detects presence of chemical or biological explosive substances in ambient atmosphere within the multireflection cell, by means of a detection algorithm based on a stored table of data that are characteristic of the substances.

* * * * *